United States Patent [19]

Pauly et al.

[11] Patent Number: 4,958,280
[45] Date of Patent: Sep. 18, 1990

[54] APPARATUS AND METHOD FOR SATISFYING DISPOSABLE CONTACT LENS PRESCRIPTIONS

[75] Inventors: Thomas E. Pauly; Jeffrey C. Van Doren; John P. Henessey; James M. Christiansen, all of Jacksonville, Fla.

[73] Assignee: Vistakon, Inc., Jacksonville, Fla.

[21] Appl. No.: 72,184

[22] Filed: Jul. 10, 1987

[51] Int. Cl.$^5$ .............................................. G06F 15/20
[52] U.S. Cl. ..................................... 364/403; 364/401
[58] Field of Search ................. 364/403, 401, 408; 235/385, 381

[56] References Cited

U.S. PATENT DOCUMENTS

| | | | |
|---|---|---|---|
| 3,770,941 | 11/1973 | Gechele | 235/385 |
| 4,567,359 | 1/1986 | Lockwood | 235/381 |
| 4,766,542 | 8/1988 | Pilarczyk | 364/401 |

FOREIGN PATENT DOCUMENTS

| | | | |
|---|---|---|---|
| 0061942 | 5/1977 | Japan | 235/385 |
| 0037661 | 3/1980 | Japan | 364/401 |
| 0121470 | 7/1983 | Japan | 364/401 |
| 8502700 | 6/1985 | World Int. Prop. O. | 364/408 |

OTHER PUBLICATIONS

"Changing Market Structures and Information Technology: Adopting New Strategies in Industrial Fasteners", Industrial Marketing Management, 1976, David W. Day, pp. 13-16.

Primary Examiner—Michael R. Fleming
Assistant Examiner—Gail O. Hayes
Attorney, Agent, or Firm—Audley A. Ciamporcero, Jr.

[57] ABSTRACT

Systems and methods are provided for the accurate, ongoing filling of prescriptions for disposable contact lenses. In a preferred system, a central ordering/inventory computer is associated with satellite PCs at which attending eye care professionals can place orders. In preferred methods, periodic serial to batcxh mode conversions merge new orders, standing orders, order changes, as well as other updates and deletions. Patient history files allow maintenance of data bases for the eye care professionals as well as for the manufacturer of lenses.

10 Claims, 14 Drawing Sheets

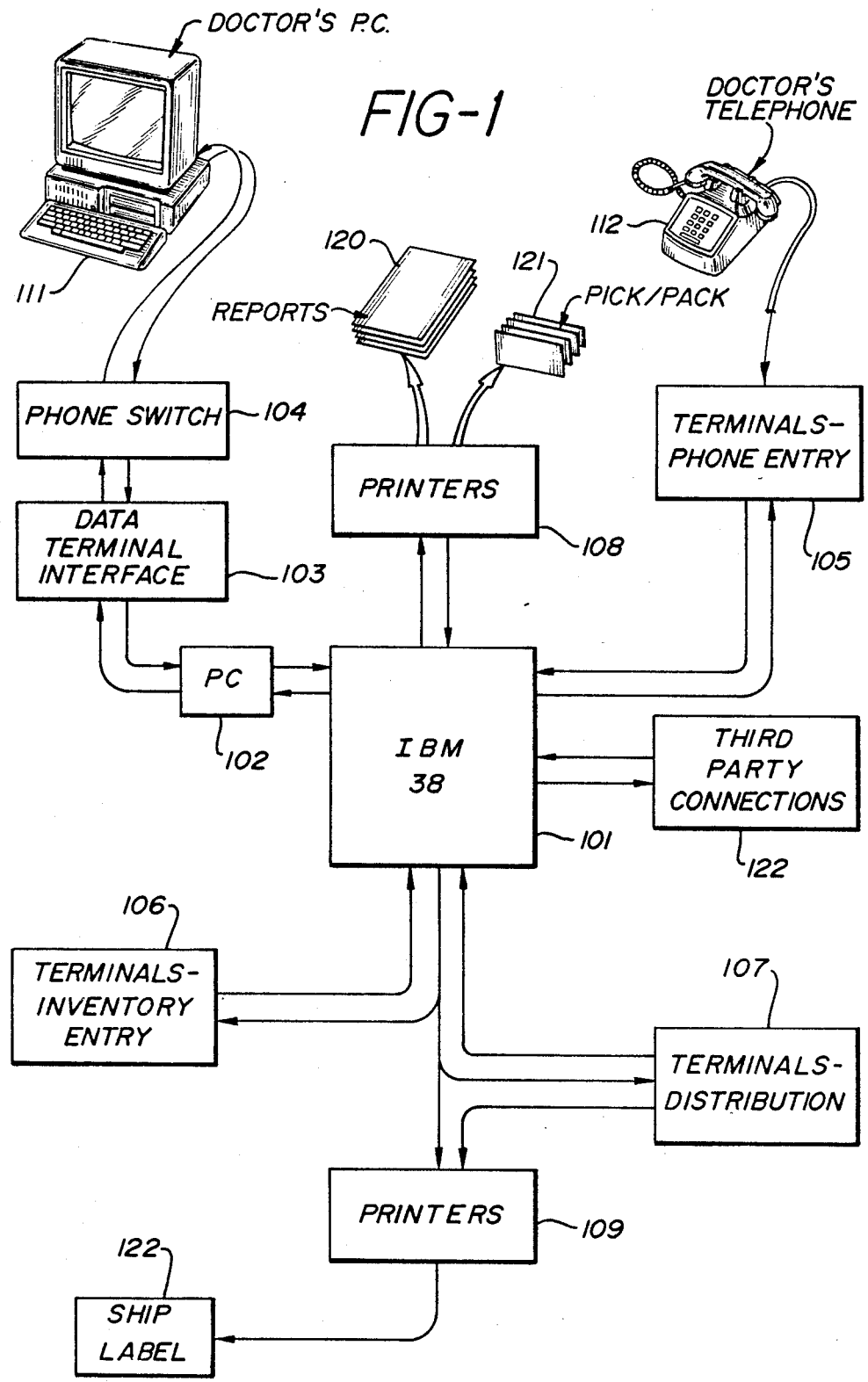

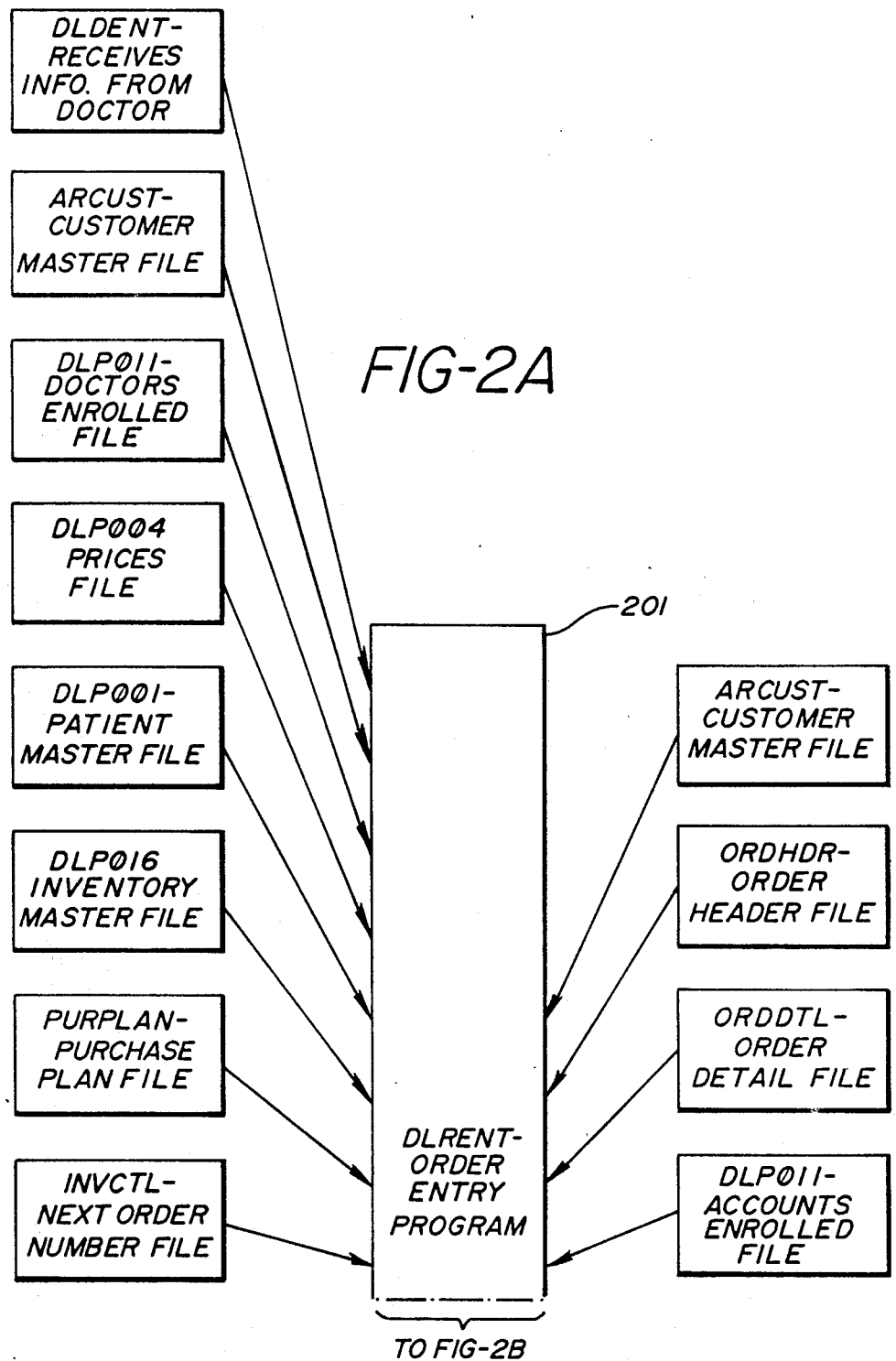

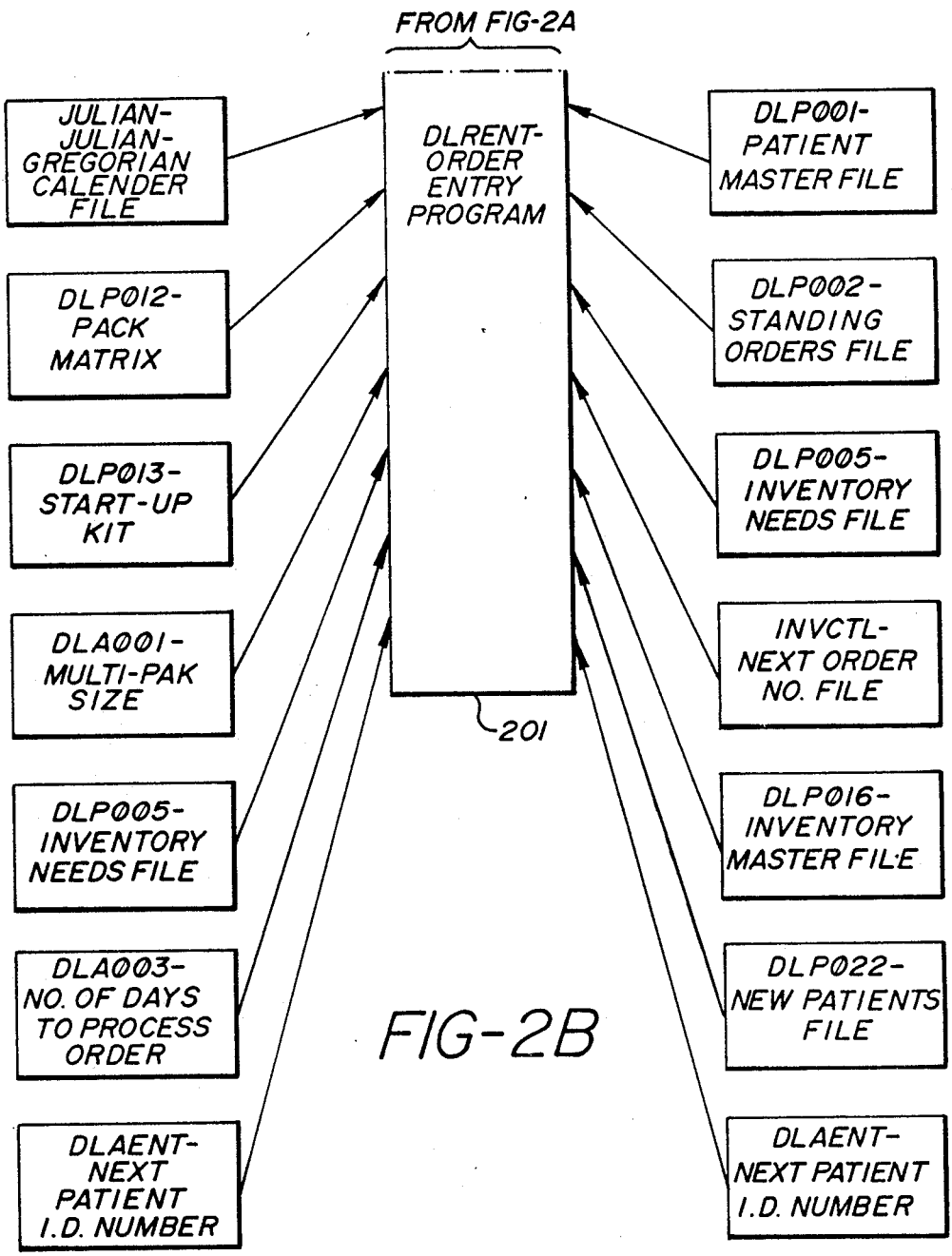

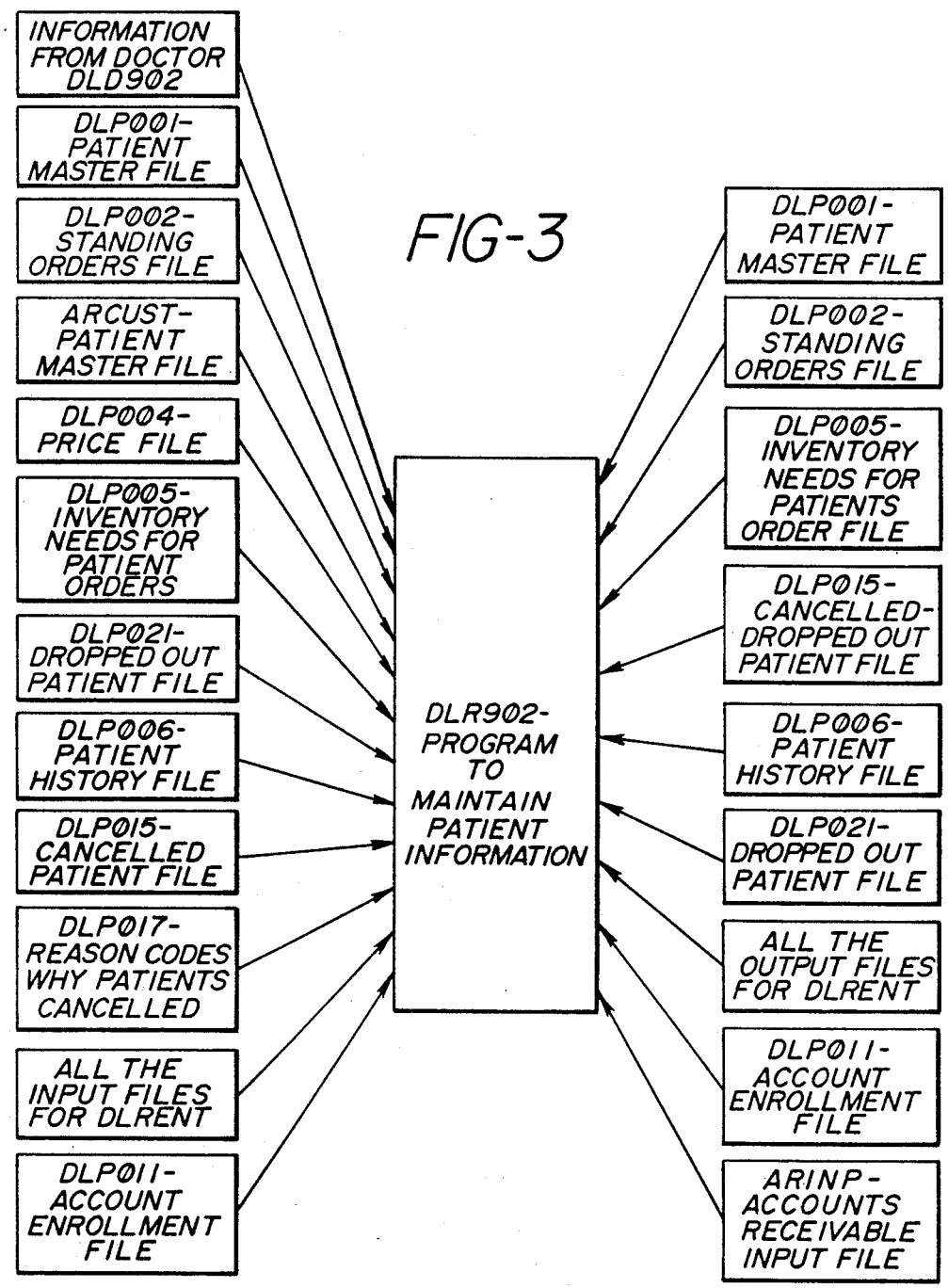

TO FIG-6B

APPARATUS AND METHOD FOR SATISFYING DISPOSABLE CONTACT LENS PRESCRIPTIONS

FIELD OF THE INVENTION

This invention relates to effective provision of contact lenses, and more particularly to the accurate and ongoing fulfillment of disposable contact lens prescriptions.

BACKGROUND OF THE INVENTION AND PRIOR ART

The supply of contact lenses poses many challenging and relatively unique requirements. Each lens, although not necessarily custom made to the eye of the patient, is characterized by a number of lens parameters each of which may vary through quite an extensive range of values. It is currently not unusual, for example, for companies in the business of production of lenses to maintain an inventory of as many as 25,000 different lathe cut toric and spherical lens types. Such companies typically maintain elaborate, labor intensive direct telephone ordering facilities, and even so, the precise requested lens is often not currently available and a doctor must choose from a number of approximately appropriate lenses which are available. Typically, the requested lenses are pulled from inventory and shipped through a convenient method, to be tried by the doctor with the patient.

The onset of disposable lenses promises to alleviate many of these problems, and yet presents still others which heretofore have not been faced. Such lenses, the production of which is taught by U.S. Pat. Nos. 4460489, 4565348, and 4495313 promise substantial reductions in the variety and total number of lens types in inventory, because of the inherent production accuracy and relatively improved predictability of lens parameters during the production process. Nevertheless, a complete inventory of spherical and toric lenses still could number in the thousands of inventory entries.

While as of the filing hereof, it is uncertain just what percentage of total contact lens users will convert to a disposable lens system, informed judgments indicate that the adoption will be widespread, and that formidable problems will be presented in supplying the needs of patients and attending physicians.

At any given time, an attending "eye care professional" (i.e. optometrist, ophthalmologist or optician) will have a panel of patients who have adopted disposable lens programs, each having a standing prescription for lenses which will include not only the standard lens parameters of base curve, magnification, etc. for each eye, but additionally the wear and replacement cycle for lenses. For example, patients may be directed to remove and replace lenses most likely on a one or two week cycle (although in the end, accumulated experience and judgment will be controlling, perhaps even extending wear cycles longer than two weeks, and in all events custom prescribed to the individual patient). Clearly, whether lenses are provided to the patient at a rate of two, six, or even ten or twenty at a time, it is highly desirable both to the eye care professional and to the patient that lenses be provided on an automatic refill basis, and that unnecessary or overly frequent visits be avoided. On the other hand, the relatively critical nature even of every day eye care demands that the eye care professional have ultimate control and discretion of the dispensing process, and hence that the eye care professional be able to create the prescription in the first instance, and be able to update or vary the prescription on such basis as medical discretion may dictate. Throughout, the reasonable expectations of both patient and eye care professional must be fulfilled respecting speedy, accurate, and satisfactory availability of lenses for purposes of initial patient fitting, ongoing lens supply, variation or alteration of prescription, and relatively minimal inventory burden upon the physician. Correspondingly, although the ultimate goal of the system is patient and eye care professional satisfaction, the normal business requirements of accurate inventory, billings, product traceability, and overall minimum cost burdens must be satisfied.

It is accordingly an object of the present invention to provide methods and apparatus tailored specifically to the requirements of disposable contact lenses. It is an associated object that such systems and methods promptly and accurately allow attending eye care professionals to maintain acclose doctor--patient relationship, and provide initial and ongoing prescription fulfillment with minimal intrusion into that relationship.

It is a further object to provide methods and apparatus which automatically supply a patient's ongoing lens requirements, as directed by the eye care professional in accordance with a prescribed replacement schedule, and to maintain associated inventory and billing procedures.

Finally, but by no means least, it is an object that such goals be met in a cost-effective fashion, thereby to minimize the price burden both on eye care professionals and on patients, and to permit effective delivery of the functional advantages inherently attendant to disposable contact lenses.

SUMMARY OF THE INVENTION

In accordance with the principles of the present invention, eye care professionals are provided alternative ordering methods, in accordance with their needs, which may vary from automated order entry through personal computers at the professional's office location, communicating through data links with central computers at the supplier, to direct telephone calls, or a variety of other forms of data communication which become economically feasible. At the central supplier's station, a variety of file storage means, which maintain appropriately configured files and in accordance with tailored system architecture, selectively process these files in accordance with the various contact lens operations, thereby effectively to manage the transaction, in some instances as individual transactions, and in others in a batch mode.

In a preferred embodiment, prescribing eye care professionals have the opportunity to phone orders directly, or through an on-site personal computer equipped with a disc drive and modem (e.g., an MS-DOS personal computer equipped with 256K main memory and a Hayes compatible modem). Orders from the on site personal computer are received at a properly adapted computer system at the central control site, where they are assembled and appropriately formatted for processing. Telephone orders are manually assembled and formatted for like processing. For a predetermined time, such as during normal business hours, orders are taken in by both routes, and are assembled into a batch. At some predetermined time, for example overnight, the day's orders are processed in a batch mode, and appropriate individual pick/pack order forms are printed. Typically the next morning, the pick/pack forms are delivered to an inventory/distribution area, where during the next day or so, orders are picked, verified, packaged and shipped to the customer. At the time of receipt of the order and again at shipping, appropriate inventory file adjustments are made. As new orders come in, separate files are maintained respecting ongoing provision of lenses to the eye care professional and/or to the patient, and these standing orders are also integrated with the long term inventory needs and the daily order filling process in a batch mode on a regular predetermined basis. Provision is also made for changes in patient information and ordering, which are also automatically integrated into the process. Thus, an important feature of the invention is that a complete patient file is maintained; optionally but advantageously, eye care professionals who employ a personal computer with modem may be provided access to such information, for purposes of their own use. Similarly, the entire process facilitates simple but effective billings on a desired periodic basis, either directly to the patient, to or through the eye care professional, or through automatic credit procedures such as credit card charges.

DESCRIPTION OF THE DRAWINGS

FIG. 1 shows a block diagram schematic system embodying the principles of the present invention;

FIGS. 2A and 2B through 9, and 11, inclusive, illustrate file processing at a central computer location for respective significant system procedures.

BEST MODE FOR CARRYING OUT THE INVENTION

Figure 4:
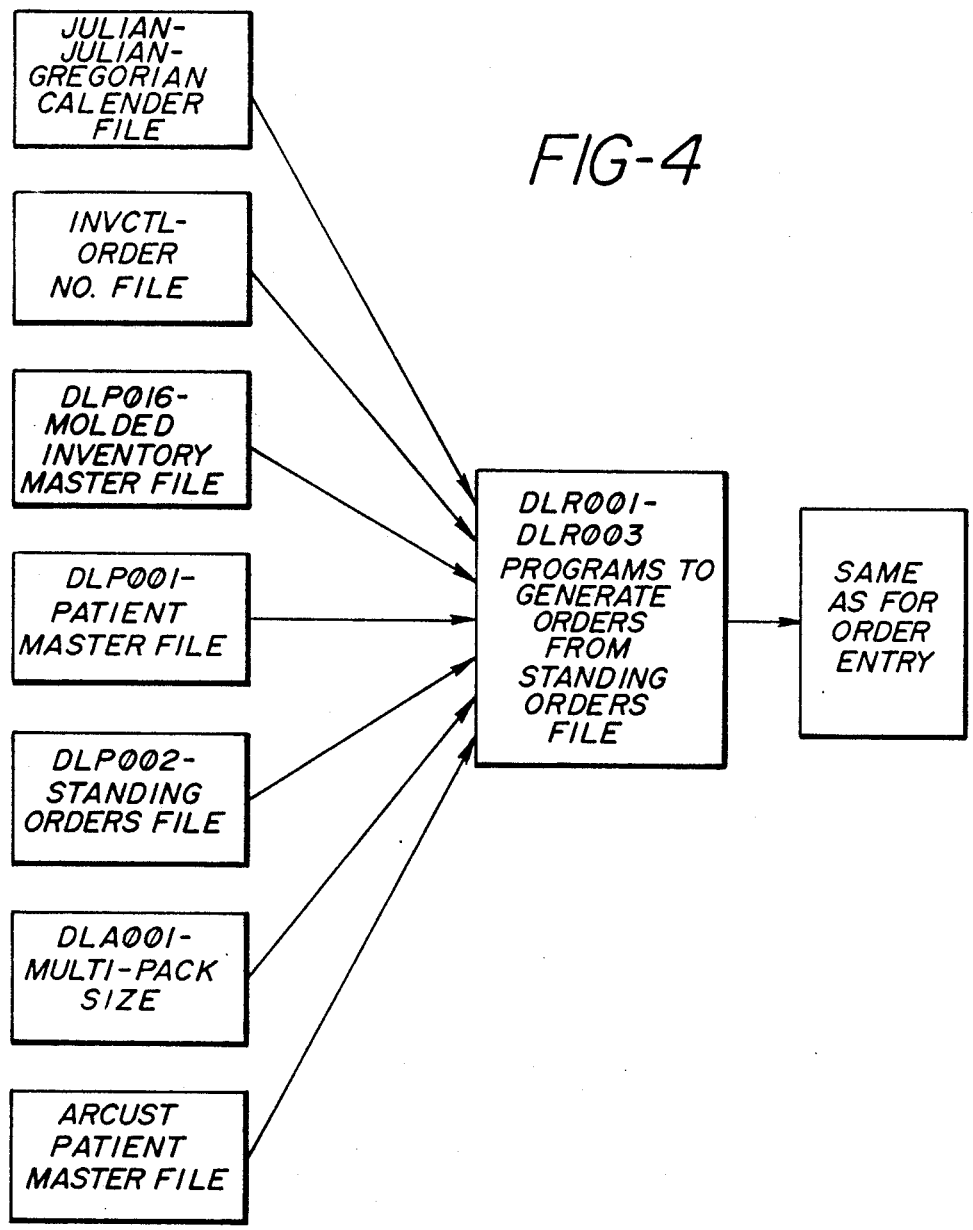

Referring first to FIG. 1, there is shown in schematic form a system embodying the principles of the present invention. For the sake of consistency but without limitation, some apparatus will be characterized as being at the "doctor's" office and others at the "company's" office, to distinguish remote operations from central ones. It will be understood, however, that these terms are not used by way of limitation or in any way to characterize specifically where such apparatus may be located, or whether the prescribing party should be a opthalmologist, optometrist, an optician, or a commercial entity involved in the business of contact lens prescriptions.

At the heart of the system is a central computer of substantial processing power, advantageously the system commercially available from International Business Machines under the trade designation of "IBM 38". This system is characterized by 16 ports, appropriate facility for local storage on disc drives or tape, and more than adequate capacity and speed for performing operations in accordance with the principles of the present invention. As shown in FIG. 1, the computer 101 is connected through associated data links to one or more local personal computers 102, a number of terminals 105, 106, and 107 dedicated to manual data input and output, appropriate printers 108 and 109 for hard copy output, and, as desired, additional apparatus for communication with other data systems. For example, shown simply as "third party connections" 122 are optionally featured interconnections, such a direct data communication network with cooperating banks or financial institutions for purposes of billings, credit card transactions, or the like financial reports.

As shown in FIG. 1, orders may be received either from a personal computer 111 at the doctor's office, or by telephone 112 in conventional fashion. In a preferred embodiment, the doctor's personal computer will be an IBM PC unit, or one of the many commercially available compatibles which employ the MS-DOS operating system, having at least 256K memory and equipped with a modem (e.g. Hayes or Hayes-compatibles) for direct data communication with the company. As shown, a telephone switching system 104 at the company will receive the data, and employ an appropriate data terminal interface 103 such that the doctor's PC 111 may communicate with a like PC 102 at the company. Two-way data communication facilitates not only the ordering process, but also many features of the invention relating to patient record storage and sharing. For example, it may be that the doctor's initial ordering inquiry will be for a pair of lenses having respective characteristics which are either temporarily or unconditionally unavailable. Since many of the lens fitting parameters are in the doctor's judgment approximate and subject to considerable judgment in the first instance, the FIG. 1 system may optionally allow the PC 102 to draw appropriate inventory information from the computer 101, and convey to the doctor's PC 111 identification of a variety of lenses which are available and which are approximately equivalent to the lenses first requested. Clearly, however, accurate prescription filling will be the goal and the normal rule, rather than near approximation based on professional discretion as in the past. This interaction between PC's 102 and 111 will facilitate an effective, individual prescription by the doctor based upon all relevant lens parameters, including those which he believes critical, and those which he believes less exacting.

The PC to PC ordering system also permits, as desired, a batch mode ordering process. In such an instance, the doctor may accumulate in memory or on disk a number of orders over a predetermined period of time, for example a day or several days. On predetermined cue, these orders may either be transmitted in batch mode to the company, or, for example at nights when phone lines are relatively more available and rates are relatively lower, the company PC 102 may make inquiry of the doctor's PC, and down load the orders which have been accumulated in the recent agreed period of time.

Finally, doctors who use a PC may be permitted to avail themselves of the patient information which will be maintained by the company as an element of operation in accordance with the present invention. As will become apparent hereinafter, effective ongoing fulfillment of lens prescriptions will require detailed doctor and patient data, specific lens parameters currently prescribed for the patient, and, as desired, patient history of lens usage. If this feature is to be offered, it may be done so either on a real time or a periodic batch basis.

Also shown in FIG. 1 is the telephone 112, for the direct phone method of ordering, not dissimilar from that presently utilized by many companies. In such systems, the terminals 105 are occupied by a number of operators who through keyboard and CRT displays have relatively direct access to the inventory files of computer 101. Direct phone communication permits these operators either to confirm orders directly, or to collaborate with the eye care professional based on perceived special needs.

The computer 101 is shown connected, through associated data links, to other terminals 106, having a primary inventory entry function, and others 107, having a primary distribution control function. Generally, although not essentially, the terminals 106 and 107 will be remote from the computer 101, being located at manufacturing and/or warehousing facilities of the company. In particular, the terminals 106 are provided so that the files of computer 101 may be appropriately updated as lenses are placed in inventory. Likewise, the distribution terminals 107 facilitate the removal of lenses from inventory of the computer 101 as orders are filled and shipped. Printers 109 operate under control of the computer 101 and/or the distribution terminals 107 to generate shipping labels 122 and associated documentation 120 in accordance with filled orders.

A transition in accordance with the preferred embodiment of the principles of the present invention between the order entry system 102 and 105, and the inventory entry and withdrawal 106 and 107 is a batch mode report and form procedure exemplified by printer 108, reports 120, and forms 121. In particular, it will be appreciated that considerations of accuracy, time, and cost will normally dictate a crossover between item and batch processing. This may perhaps be better appreciated when one considers that the total U.S. market, and hence manufacturing output, in non-disposable soft contact lenses may until recently have been in the range of twenty to twenty-five millions of lenses. Based upon conservative market projections, however, if only a small percentage (e.g. 10) of these patients are converted to disposable lenses on a two-week wear cycle, many more millions of disposable lenses will be required on an annual basis just by disposable lens users. Thus, the labor intensive, and relatively inexact item by item scheme of processing orders to final shipment cannot possibly work in this circumstance, and a batch mode conversion is desirable.

It is therefore contemplated, in preferred embodiments, that order entry continue on a relatively individual basis, thereby permitting doctors to be truly interactive in the order process, and to be placing orders based on lenses actually available, rather than upon a set of theoretical parameters which may not be met. In preferred embodiments of the present invention as described hereinafter, this item to batch conversion will be made after each business day, and will be accomplished through the generation of custom pick/pack forms 121, which will be physically conveyed to the distribution facilities, and used for the picking of lenses from inventory, the packing of lenses for shipment, and the generation of appropriate shipping labels. Beneficially, this conversion to batch mode will facilitate the integration of new orders, changed orders, and fulfillment of standing orders, without discrimination from the standpoint of order filling and distribution. As also shown in FIG. 1, the printers 108 are properly dedicated to the generation of reports 120, which may be simple hard copy verification records as well as billing statements and the like.

It is first beneficial to provide functional summaries of key processing routines which are routinely employed in preferred embodiments of the principles of the present invention. In the following, "molded" is used interchangeably with "disposable", in view of the preferred method of manufacture as indicated by the patent citations hereinbefore. Clearly, however, the lenses may be made in any way desired by the manufacturer. The key programs are:

1. An order entry program - "DLRENT". This program receives all orders for products (orders for product made in different procedures may be different options on a menu). It will take stock orders, patient orders and start-up orders from doctors. When an order is generated, this program writes to two order files (the order header file and order detail file) and updates the customer master file and inventory master file.

If a doctor gives a patient order, an order for two introductory multi-packs is immediately generated (the sku's are the same as those of the patient's). The order for introductory lenses will have a comment associating the order with the patient last name, patient I.D. number, and patient order number.

The order for the first shipment of lenses to the patient will be generated or not depending on the given arrival date for the first shipment. If the arrival date for the first shipment is less than 14 calendar days from present, DLRENT must specify special handling. Generally, the patient's arrival date will be at least 2 working days from "now". Patient information is saved at this time. DLRENT will write to both the patient master file and the standing order file. If a patient's first shipment is to be sent out immediately, information is written to the two order files and the order number is recorded in the patient master file. For a patient order, the doctor either gives a complete address or just the patient name (the last name could be a series of numbers). If the patient's lenses are to go directly to the patient, a complete address is required.

DLRENT will also write into file the inventory needs for future patient shipments when patient orders are taken. Most desirably there will be needed no check of availability of lenses; the number of lenses on order will be increased when orders are actually generated.

This program will also be used to enter orders received in the mail. The difference is that if an order comes from the mail, the patient ID no. is entered; if order comes via telephone or PC, the patient ID no. is assigned by the computer. The patient ID number will typically have a check digit.

This program also employs credit security features. For example, if the doctor's orders are COD only because of credit problems, the doctor will not be allowed immediately to order lenses. If the doctor has any credit problems, stock and new patient orders will not be allowed (although usually, standing patient orders will be allowed). Patients needing lenses for one eye only will appear as needing lenses for both eyes, in this system; that is, the prescription for the right and left eyes will be the same. A one week wearing schedule will thus be entered as two weeks; otherwise, the patient will get twice as many lenses as really needed.

When a patient order is taken, the patient is added to the file which lists new patients (for a special mailing to welcome new patients). When a patient order is taken, the information about numbers of patients is changed in the account enrollment file. Start-up kits will be designated differently from other orders for lenses to allow tracking of orders.

2. A program to display or change information saved for patient; also used to cancel or re-enroll a patient -"DLR902".

Logically, a patient can be cancelled only if there is a standing order for that patient; a patient can be re-enrolled only if there are no standing orders for that patient; and changes can be made only if there is a standing order. A customer service representative will be enabled to search for the patient data if provided the doctor's number and at least the first letter of the patient's last name. It is desirable, although not essential, to have ready access to the last order number and the last shipment date for a patient.

In accordance with the present invention, it will be possible to change wear schedule or shipment schedule. This may entail a charge, so the program may write a record in a file, "ARINP". The patient schedule will be set up for a complete year, the doctor will specify arrival date for first shipment, and the doctor will not receive introductory lenses as result of such change. Both the standing orders file and the file of inventory needs for future patient shipments will be updated accordingly. Also, the information about the number of patients in the account enrollment file will be changed. Wear and shipment schedules will normally not be allowed to change if doctor has a credit problem.

It is desirable for management purpose to track cancellations, and hence the reason for cancellation may be obtained. This program will place the reason and patient information in a cancelled/dropped-out patient file (the record may have a record code to distinguish a cancelled patient from others), remove any standing orders for the cancelled patient, update the file of inventory needs for future patient shipments, and update the information about the number of patients in the account enrollment file. This will entail a charge, so the program will write a record in file "ARINP".

When patient is re-enrolled or cancelled, a record of the total number of lenses the patient was shipped and the total number of shipments during a previous period will be in the patient history file.

When a patient is re-enrolled, an order for two introductory multi-packs for the doctor will be generated, and the patient master file, the standing order file, and the file of inventory needs for future patient shipments will be updated. The patient will also be removed from the file listing the dropped-out patients.

If the prescription or the first shipment arrival date is changed, the file of inventory needs for future patient shipments will be changed. If the change provides that shipments now go to patient, rather than to the doctor, it is important to have a complete address. The doctor gets no introductory lenses in this case.

3. A set of programs to generate orders for patients so they will receive their next shipments on time; also to identify drop-outs for the monthly patient management report -- "DLR001, DLR002, DLR003".

This program set will write to the orders files and update the customer master file and inventory master file on the basis of the standing orders file. As appropriate, the record in the standing orders file triggering the order will be deleted and written in a backup file and kept for a day or two. The number of days to look ahead will be in a data area, e.g. 5 days. Preferably, but not essentially, there will be no check of lens availability. If a doctor has a credit problem, orders will nevertheless be generated. If there are no more standing orders for that patient, the patient will be added to the list of drop-outs used for the monthly patient management report.

4. A program to generate a picking/packing document -"DLR0015".

The invoice/order number will be preferably barcoded.

For ease of handling, it is desirable to group different types of orders--stock orders requiring two or more pages, stock orders requiring one page, patient orders going directly to patient, and patient orders going to doctors. This program will be able to identify exceptions (overnight deliveries) so a packing slip can be generated early in the afternoon. It will be able to produce a packing document for a given order.

If the doctor has credit problems (is on hold or all orders are COD), packing documents for stock orders will not be generated (documents for patient orders will be). This program will not check inventory availability.

5. A program to use when actually shipping the lenses (shipping program) -- "DLR990".

This program checks that lenses having correct parameters have been picked; to do so, the program uses the file associating lot number with sku. The program records that the given lot number went to each particular doctor; to do so, it uses the molded inventory detail file. It also prints labels.

The label will preferably have a barcode e.g. employing an invoice number, a zip code, and a check-digit.

The program will also write a record to the reports file so the monthly patient summary file can easily be generated. This program writes to the shiplog file and writes records to the file "ARINP" to reflect sales tax charges and special handling charges. It also keeps track of the multi-packs sold, itemized by parameter, and it updates the patient master file with shipping date and order number. If the customer master file indicates it is appropriate to do so, a record will be written to a special invoices file so that "bill-to's" can receive a report at weeks end regarding the orders of their "ship-to's".

This program will also enable customer service representatives to cancel orders.

6. A program to generate at month-end a report for the doctors stating the patient orders shipped "this" month, the patient orders to be shipped in the next two months, the patients who will drop out "next" month, the patients who dropped out two months ago (if they have not been re-enrolled), and the patients who dropped out four months ago (if not re-enrolled) -- "DLR501".

This program will read the standing orders file for the next two months of shipments to identify patient shipments to be made in the next two months. It will read the reports file to get the patient shipments made this month, and will read the file listing the drop-outs to identify patients that should appear on the reports.

7. A program to report weekly to bill-to.s the sales activity of their ship-to's, if requested by bill-to. Report will show weekly sales, month-to-date totals and year-to-date totals.

This program will obtain sales for the instant week from the bill-to-report file. It will also obtain month-to-date and year-to-date totals from account enrollment file.

8. A program to process credits issued by sales representatives.

This program is standard current procedure, and employs straightforward data entry and storage.

9. A program to protect safety stock (or maintain a future shipments file; it states how many lenses of each sku are needed for patients for each of the next 12 months) -- "DLR903".

The file of future inventory needs is loaded/updated by the molded order entry program and by the program for changes to the patient master.

This program also displays, for each sphere power, the number of lenses in inventory and the number of lenses on order.

10. A series of programs to generate periodic (e.g. monthly) management/sales reports. These are straightforward, and include:

a. Dropouts (this month, two months ago, four months ago) by doctor and territory -- "DLR503".

b. Patient cancellations (this 3-month period, last 3-month period, and last 12 months) by doctor and territory -- "DLR700".

c. New patients this month, total number of active patients, and in each case a breakdown by shipping schedule and wearing cycle -- "DLR508".

11. Program or programs providing pricing for separate contract orders--"DLR921".

These programs will enter price contracts for a given account. They will report all price contracts, report contracts just entered, and report expired contracts. Each change, addition, and deletion of a contract are noted in a price log file, and the contents of this file are reported and then emptied each day.

12. Additional programs:

a. Program to remove patients from patient master file 6 or 8 months after end of their respective enrollment period.

b. Program to clear the month-to-date information in the account enrollment file at the end of the month.

c. Program to clear the year-to-date information in the account enrollment file at the end of the year.

d. Program to allow customer service representatives to view orders already generated and learn the status of these orders, picked, shipped, etc. The representatives will also be able to confirm prescriptions as well as ship-to addresses.

13. A series of programs allowing entry of the number and sku of lenses in a batch as the lenses "are placed in inventory".

These involve a molded inventory detail file used to track shipments, some programs reporting placing lenses and adjusting lenses in inventory, and a program to allow inquiries regarding sphere power.

In partial summary, a number of separate programs provide the basis of detailed execution of the principles of the present invention. It is therefore apparent that in accordance with the present invention, file organization and file processing are important considerations and concerns. Following are definitions of key files, the processing of which also define procedural aspects of the present invention.

A. DLP001- This is the complete patient master file, which defines the variables associated with the patient. The patient is identified by name, last, first, and middle initial, address, and the prospective point of shipment, i.e. through the doctor or to the patient. The file contains enrollment data, both beginning and end. Relevant data for the lenses are provided, including base curve, diopter correction, and other relevant attributes.

The file also contains use and shipment data, including wearing interval, quantity per eye in each shipment, date of any changes from the doctor, and the like shipping information. This file is loaded by the program DLRENT, and is updated by the program for changing patient master information and the molded shipping program.

B. DLP002- This file is the standing orders file, is coordinated with the associated patient entry in DLP001, the patient master file, and provides the date of next shipment, the quantity to be shipped for each eye, and the price of the lenses to be shipped. This file is loaded by the molded order entry program and is updated by the program for changes to the patient master file.

C. DLP003- This file is the monthly patient report file, is coordinated to DLP001, and contains a report of shipments to the patient (by doctor number and patient I.D.). This file is written to during the current month when a patient order is shipped, and again at month's end when shipments for the next two months are identified.

D. DLP004- This is the price file, and provides pricing information.

E. DLP005- This file defines inventory needs for standing patient orders, and has variables for each lens, by base, diameter, and sphere, for a number of months in advance, for example twelve months. It is updated by the molded order entry program and the program changing the master file.

F. DLP006- This file contains a running history of accounts cancelled and re-enrolled, is coordinated with the patient master file, and defines enrollment and dropout dates, total enrollment shipments, and individual numbers of shipments. Provision is made for explanations of transactions.

G. DLP007- This file identifies batch numbers and thus functions as a master file. It also defines various parameters of the lenses, including the lens code number itself, and the parameters of base curve, sign and diopter power, axis, prism, diameter, water quantity, quantity in inventory, packaging information, expiration date and the like variables. This file is loaded and changed by the program allowing the user to place lenses in inventory and take lenses out. Its main purpose is to define batch control identification. It is used by the shipping program to fetch lens specifications associated with the entered lens number.

H. DLP008- Molded Detail Lens File. This file tracks every multi-pack shipped, associating it with order number, bill-to, ship-to, etc. It is used for recall and product tracing purposes.

I. DLP009- This file, the molded lens transaction file, is maintained to track inventory transactions, and accordingly identifies manufacturing batches as they are placed in inventory.

As such, it is similar to file DLP007, except for allocation quantity, which is not present here, and date, time, and person placing lenses in inventory, which are not present in DLP007. It is a log of adjustments to inventory.

J. DLP010- This file is the price log file, and reflects alteration of the price file DLP004. As such, it is basically a price transaction file, and is used to report additions, deletions and changes to DLP004.

K. DLP011- This is the account enrollment file, and identifies accounts who have purchased a start-up kit and contains summary information regarding sales (including special handling charges and taxes) and patient enrollment (including patient wear cycle and shipping schedule). This file is initially loaded and updated by the order entry program. Patient information is changed by the program allowing changes to the patient master. Sales information is changed by programs producing the report to bill-to's about ship-to activity. This file is used for monthly patient enrollment analysis and for a weekly bill-to sales report. It is also used by the order entry program to determine eligibility to place patient or stock orders.

L. ORDHDR and ORDDTL - This are both orders files, the former, or header file, containing all general data respecting orders and the latter, the order detail file, providing similar line item detail. As such, both files entail entries which totally characterize the order process, and hence have variables corresponding to substantially all relevant information also resident in the other, individual category files.

M. ARCUST - This is the customer (i.e. doctor) master file, and provides all requisite information concerning the doctor, including all relevant address and telephone information, and additionally, sales and marketing information including customer liability status, discount rates if any, charges and payments to date, discounts to be allowed, and so forth. Optionally but desirably, this file contains all such information on a periodic such as monthly basis extending a desired time in the past.

N. DLP018- This is the shipping log file, and contains information concerning the actual shipment of the order. As such, its primary purpose is to trigger accounts receivable processing of the other associated files when a shipment actually has been completed.

O. DLP015- Cancelled/dropped out patient file. This file contains all the information regarding cancelled and dropped out patients. It is loaded by the program allowing a patient changes and by the program removing dropped out patients from the master file.

P. DLP022- New Patients File. This file will enable the company to identify the recent new patients for various reasons, including a mailing to welcome them into the program.

Q. DLP021- Dropped-Out Patient File. This file is a list of patients with no standing orders (i.e. patients who have been sent all their lenses).

R. DLP023- Bill-To Report File. This file records shipments to ship-to's so that a weekly report to bill-to's can be generated. Information will be placed in this file on special request from bill-to.

S. DLP016- This is the inventory master file, and comprehensively defines all inventory which is available. It is used by the molded order entry and shipping programs and by the inventory inquiry programs.

T. ARINP - This is the accounts receivable input file. It identifies the various charges against the doctors.

As will be apparent from the foregoing list, while many aspects of file organization are subject to the discretion of the system architect, the relative contents of each are dictated by the overall system requirements and goals. Efficiency of processing, in accordance with the following, will also be facilitated by selection and organization of files as set forth above. Referring next in sequential fashion to FIGS. 2A through 11, classes or types of process in accordance with the principles of the present invention are defined. It will be appreciated that those of ordinary skill in the art, given the foregoing program descriptions and file and variable definitions, and the processes set forth in Figs. 2 through 11, inclusive, will in substantial measure be able, without undue experimentation, to fashion a working embodiment of the principles of the present invention.

FIG. 2 (representing FIGS. 2A and 2B when joined as shown) sets forth program DLRENT schematically, that is, the order entry procedure. To the left of the "order entry" process box 201 are files which bear data useful for or needed in the process, and to the right are files which will receive the data so processed. Generally, the order entry process will require information received from the doctor, by mail, telephone, automated PC ordering, or the like. The file DLP011, indicating doctors who are enrolled and who are eligible so to order, is called to verify the acceptability of the order.

Assuming eligibility, the customer master file ARCUST is accessed, which will provide full information concerning the doctor. In order actually to process an order, the inventory master file DLP016is called, to determine relative availability of the lenses desired to be prescribed by the doctor, and, finally, assuming that the order is to be entered, the price file DLP004is called. Based on the foregoing, if an order is to be entered, the succession of files to the right of FIGS. 2A and 2B must be updated. That is, given that an order is to be entered, the complete ongoing prescription must be provided for purposes of the doctor or customer, the patient, and the standing or ongoing procedures for the company to be able so to fill orders.

Accordingly, the customer master file ARCUST is updated to reflect new charges against the doctor's account. The inventory master file DLP016is decremented, so that the lenses needed for the immediate order are eliminated from consideration for subsequent orders, even though the order will not be filled until the time of batch mode processing, for example within a day or more of receipt of the order. In view of the unique nature of disposable lenses and prescription filling in accordance with the principles of the present invention, the standing orders file DLP002receives an entry, so that at predetermined times in the future, the patient's order will be called up and incrementally filled so that patient is insured an ongoing and ready supply of lenses in accordance with the prescribed wear schedule. Likewise, the future inventory needs file is augmented, so that ongoing production planning will be able to account for anticipated orders to be met in the standing orders file DLP002. A patient master file DLP001is created, thereby to establish a future reference for all aspects of the process respecting this patient, and the order files ORDHDR and ORDDTL are updated for immediate conversion to batch mode processing and prescription filling at the next available predetermined time. The balance of files shown in Figs. 2A and 2B are used in accordance with the foregoing, as will be evident to those of ordinary skill.

In summary, the order entry process set forth in FIGS. 2A and 2B consists of a verification that the prescribing doctor is eligible so to prescribe, a verification of the lenses ordered, and an indication of the ultimate price thereof. Completion of the order entry procedure triggers immediate and long-term order and inventory adjustments, and creation or updating of detail files respecting the doctor and the patient.

Referring next to FIG. 3, there is shown program DLR902, a sequence of processing used to maintain and to achieve alteration of the patient information. For example, in the ordering process set forth in FIGS. 2A and 2B, respective right and left lens parameters as well as lens wearing and disposable cycles are provided. Conventionally, patients' needs may change, and mechanism is provided for substantially automatic and ready alteration of the standing prescription, and appropriate adjustment of all requisite files. Accordingly, referring to the left portion of FIG. 3, the change information is received from the doctor, again by telephone, mail, PC, or the like. As in the initial ordering process, the eligibility of the prescribing doctor must be checked, from file DLP011, and, once verified, the doctor or customer file ARCUST is provided with all detailed customer information.

As in the initial ordering, the inventory master DLP016 and price DLP004 files are called up. Unlike the initial ordering stage, however, the patient information is maintained in a file on hand, DLP001, and this file is utilized for a base of information and for the actual change.

Thus, the rightmost portion of FIG. 3 indicates the files which must be updated or created. As in the initial ordering case, patient master DLP001 and doctor ARCUST files must be updated, standing orders and future inventory needs must be adjusted, immediate orders ORDHDR and ORDDTL may or may not be required, depending upon the nature of the change, and the patient master file DLP001 must be adjusted. To account for the eventuality that the change is in fact a cancellation or withdrawal, an appropriate entry may be made in the cancelled patient file. Again, coordinated use and updating of the other files shown will be self evident to those of ordinary skill.

In summary, then, the patient change procedure set forth in FIG. 3 is similar to the initial order procedure set forth in FIGS. 2A and 2B, except that additional file changes may be entailed in the nature of patient history and cancelled patient file entries.

Referring to FIG. 4, there is shown a schematic view of the standing order processing, that is, programs DLR001- DLR003. As will be appreciated, advantageous conversion from serial processing to batch mode processing occurs on a frequent, periodic basis, for example at night after each regular business day. Since standing orders, in the form of the standing order file DLP002, are always available, substantial discretion is provided for entry of the standing orders into the overall supply process. Optionally, therefore, the standing order process may be integrated with inventory surplus and backorder conditions, so long as, in all events, patients receive prescription refills adequately in advance of depletion of their standing prescription. It will be appreciated from inspection of FIG. 4, that all file data attendant to any ordering (i.e. ARCUST, DLP016, DLP001, DLP004, and DLP011) are to be invoked. The new element of the FIG. 4 procedure is the standing order file DLP002. It will be appreciated from FIG. 4 that all of the right-hand files, into which data is written, are the same as those set forth in FIGS. 2A and 2B, respecting the initial order entry procedure.

In summary, the standing order procedure is in form the same as an initial order procedure, except that the prescription information is drawn from the standing order file, and patient master file, rather than from an initial and perhaps discretionary order from the doctor. The key attribute of the standing order procedure in accordance with the principles of the present invention is that standing orders are filled on a substantially automatic basis based on the need for refilled prescriptions, subject to optional variation based on inventory conditions. In all events, standing order filling is coordinated with the serial to batch mode processing.

Figure 5:
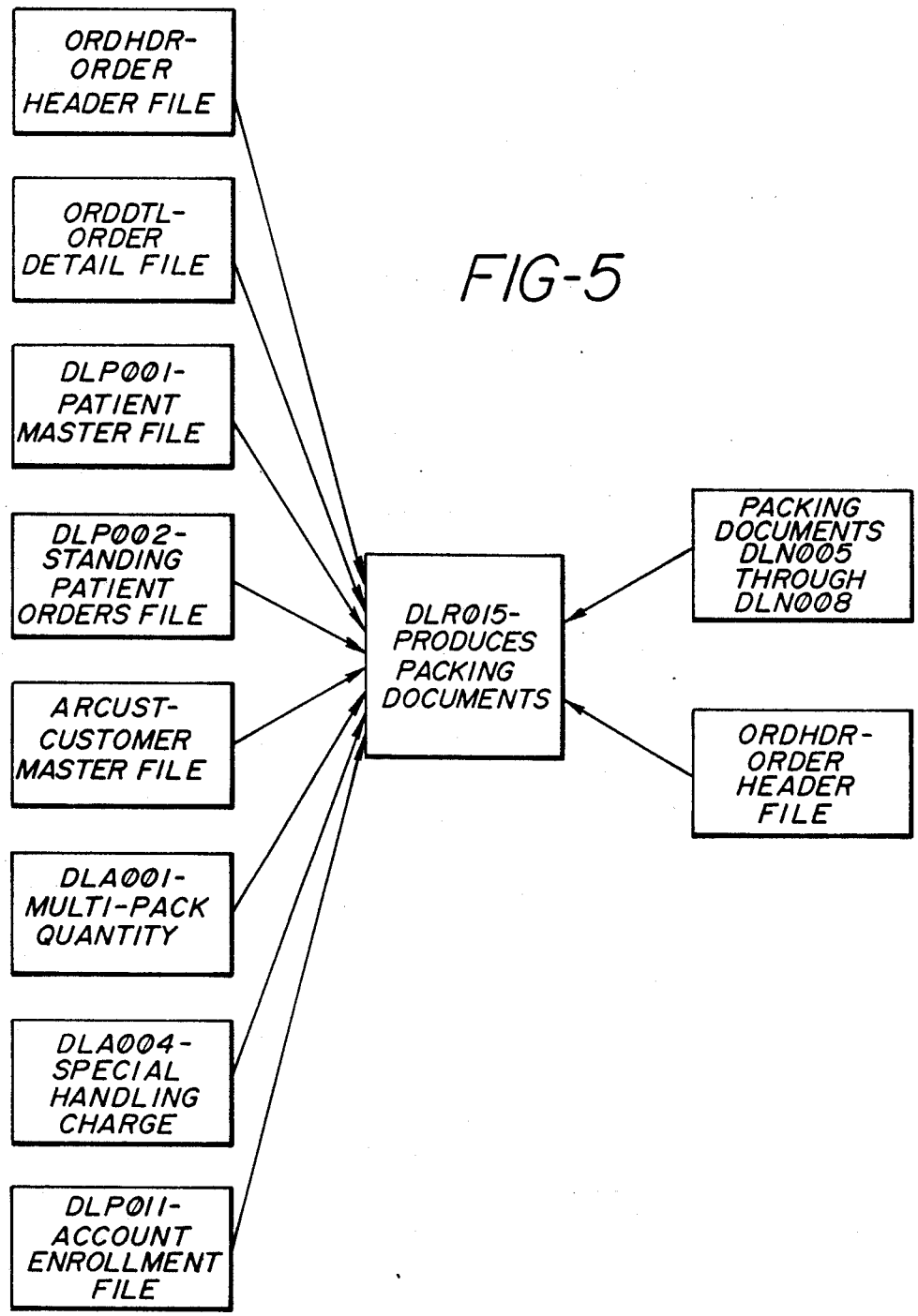

Referring next to FIG. 5, there is shown in schematic form program DLR015, the file processing used for the serial to batch conversion.

As set forth hereinbefore, this procedure advantageously generates a series of pick/pack slips, which physically represent not only the transition from serial to batch, but also the transition from pure processing to physical inventory handling and distribution. Accordingly, the ORD order files ORDHDR and ORDDTL generated in the processes set forth in FIGS. 2A and 2B, 3, and/or 4, are processed, and individual pick/pack slips are generated, for example at printers 108 of FIG. 1. Likewise, the ORD files are marked indicating the generation of pick/pack slips, and are ready for the subsequent processing. Advantageously but not essentially, the pick/pack slips 121 as generated in FIG. 5 will include computer bar codes, allowing the order filler personnel to use automated or semi-automated verification of order fulfillments, in accordance with known apparatus and procedures. Also optionally but advantageously, the pick/pack slips 121 may be segmented into different parts, with respective parts being detachable and collated in accordance with various aspects of the shipping process, thereby providing yet another self-verification aspect of systems in accordance with the present invention.

Figure 6A:
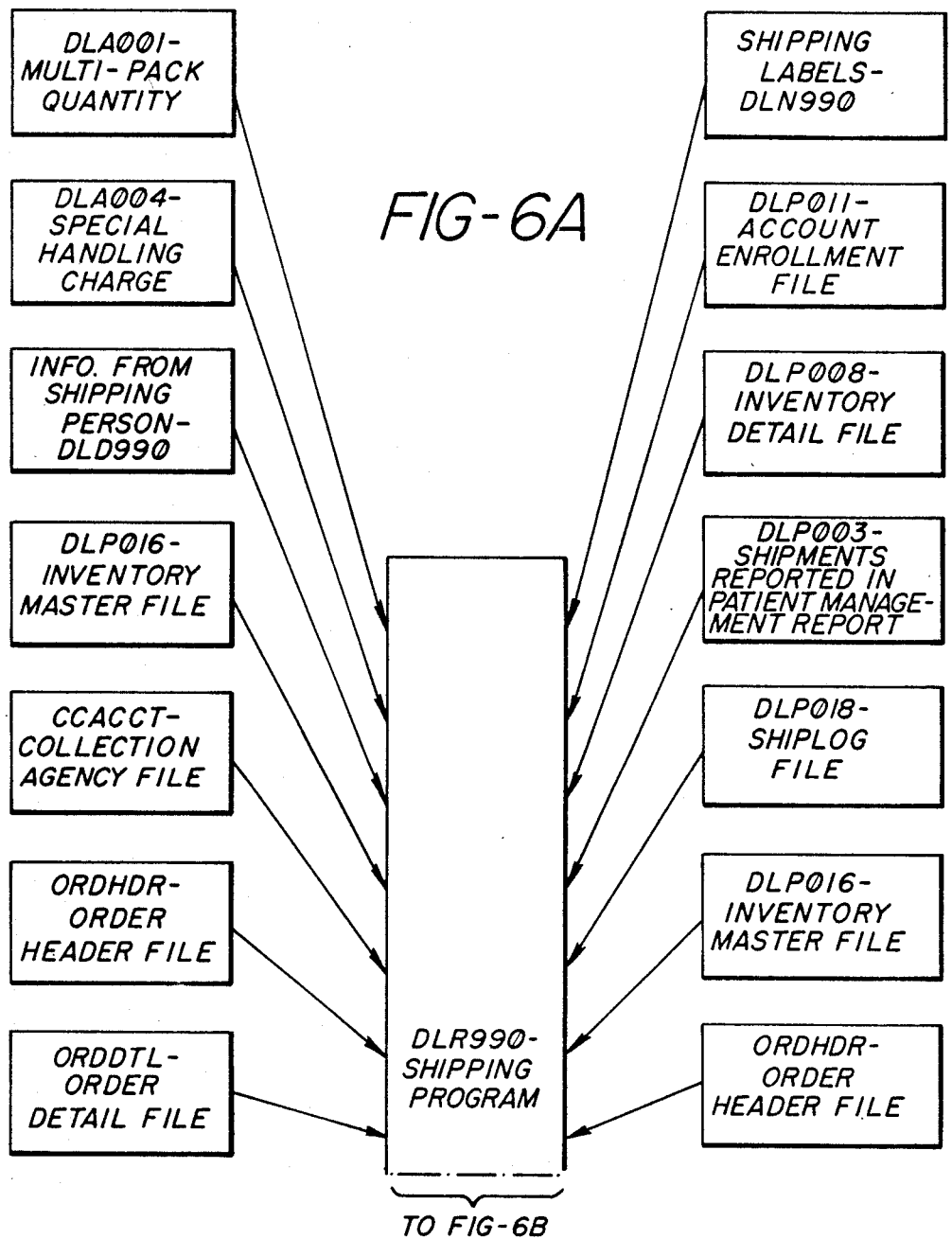
Figure 6B:
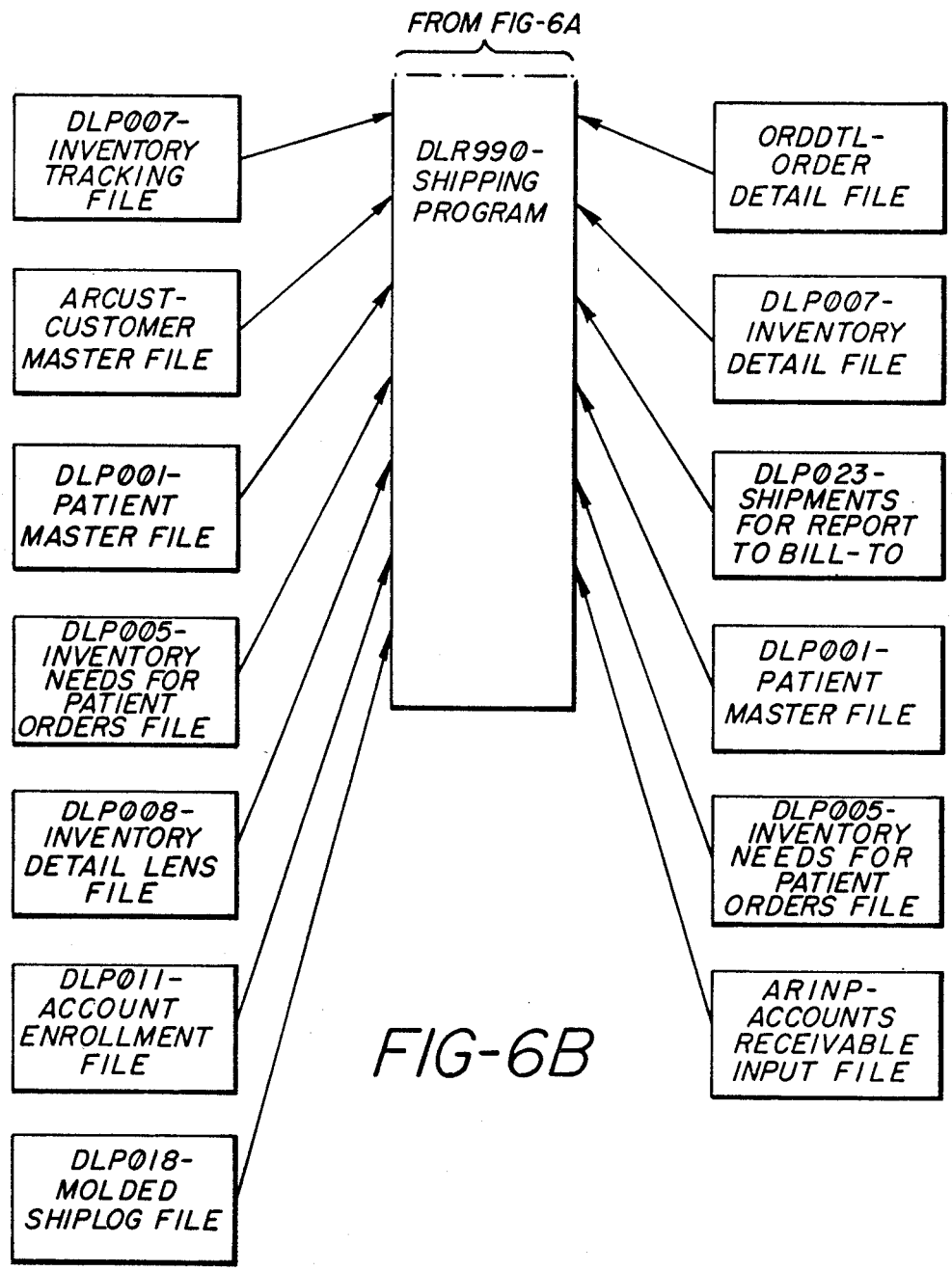

In FIG. 6, (representing FIGS. 6A and 6B when joined as shown) the shipping process of program DLR990 is outlined. Typically, this process is conducted during the work day which follows the processing of serial to batch, and the conversion to physical handling conversions as defined in accordance with FIG. 5. In FIGS. 6A and 6B, respectively associated processing steps are set forth, it being understood that the physical pick and pack process will be discharged in accordance with customary practices, the principal difference in accordance with the present invention simply being the ultimate flexibility in pack sizes and individual order quantities.

On the leftmost portion of FIGS. 6A and 6B, the order files ORDHDR and ORDDTR are again accessed, providing a verification of the lenses against the actual order. As set forth on the right, a match of the packing slip bar code and the individual packs' bar codes will result in a shipping label which contains a bar code of the zip code, and invoice/order number. Likewise, the files associated with a satisfied order must be so designated, including the inventory master DLP016, the patient master file DLP001, the molded inventory detail file, the order files ORDHDR and ORDDTL, and by no means insignificantly, the ship log file DLP018.

Thus, as will be seen from FIGS. 6A and 6B, and particularly the collection of files shown at the leftmost portion, all relevant data is available to establish comprehensive shipping, in particular including data relating to the patient, the required product, inventory and account information, and that information necessary to establish charges. Upon execution of the shipping program, then, the rightmost column sets forth the files which must be updated to indicate shipment, and the shipping labels themselves. It will be evident, based upon the foregoing detailed description of the shipping program and of the various files, that these files to be updated include, as will be appreciated, those relating to the patient master file and inventory needs, inventory and order master and detail files, and patient enrollment and accounts files. Likewise, data necessary for the patient management reports is provided, and, by way of hard copy, the shipping labels themselves.

In summary, upon execution of FIG. 6A and 6B, the physical process of lens shipping is enabled.

Figure 7:
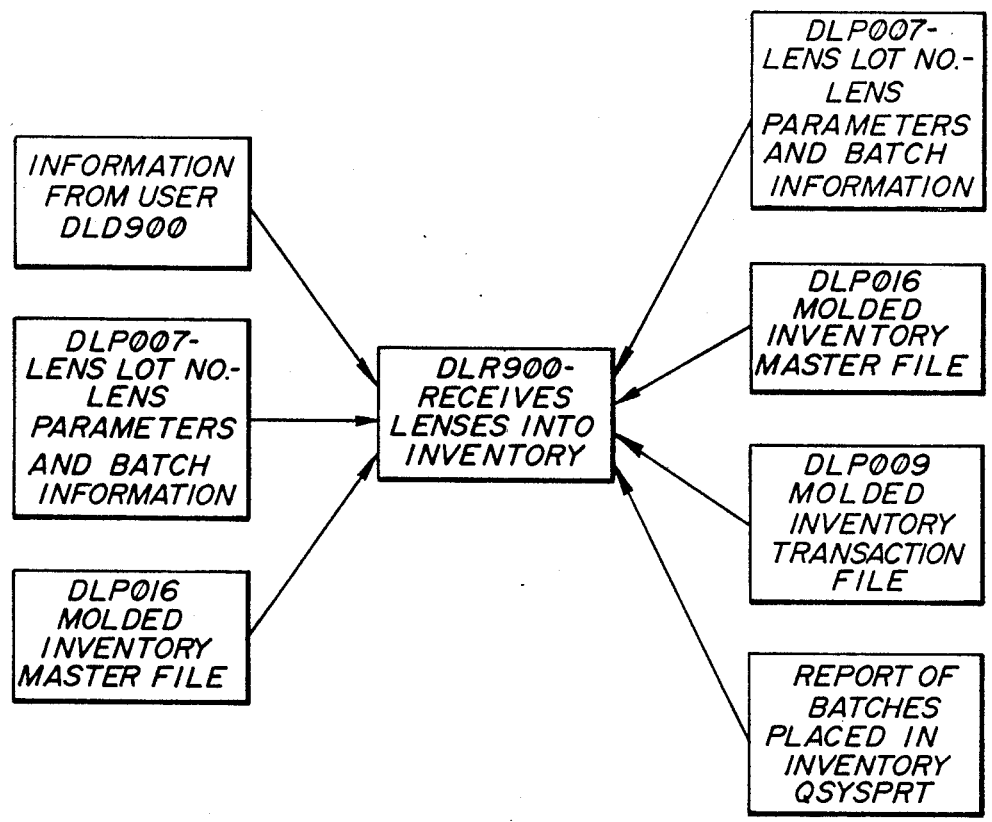

FIG. 7 shows a system flow chart for program DLR900, which receives lenses into inventory. Accordingly, on the leftmost column, the collected inventory information is provided, including file DLD900, information from the user, DLP007, lens parameters, lot number, and batch information, and DLP016, the molded inventory master files.

The execution of program DLR900, upon which the lenses are in fact entered into inventory, triggers the updating of files DLP007, DLP016, and DLP009, as well as a report of the batches placed in inventory.

Figure 8:
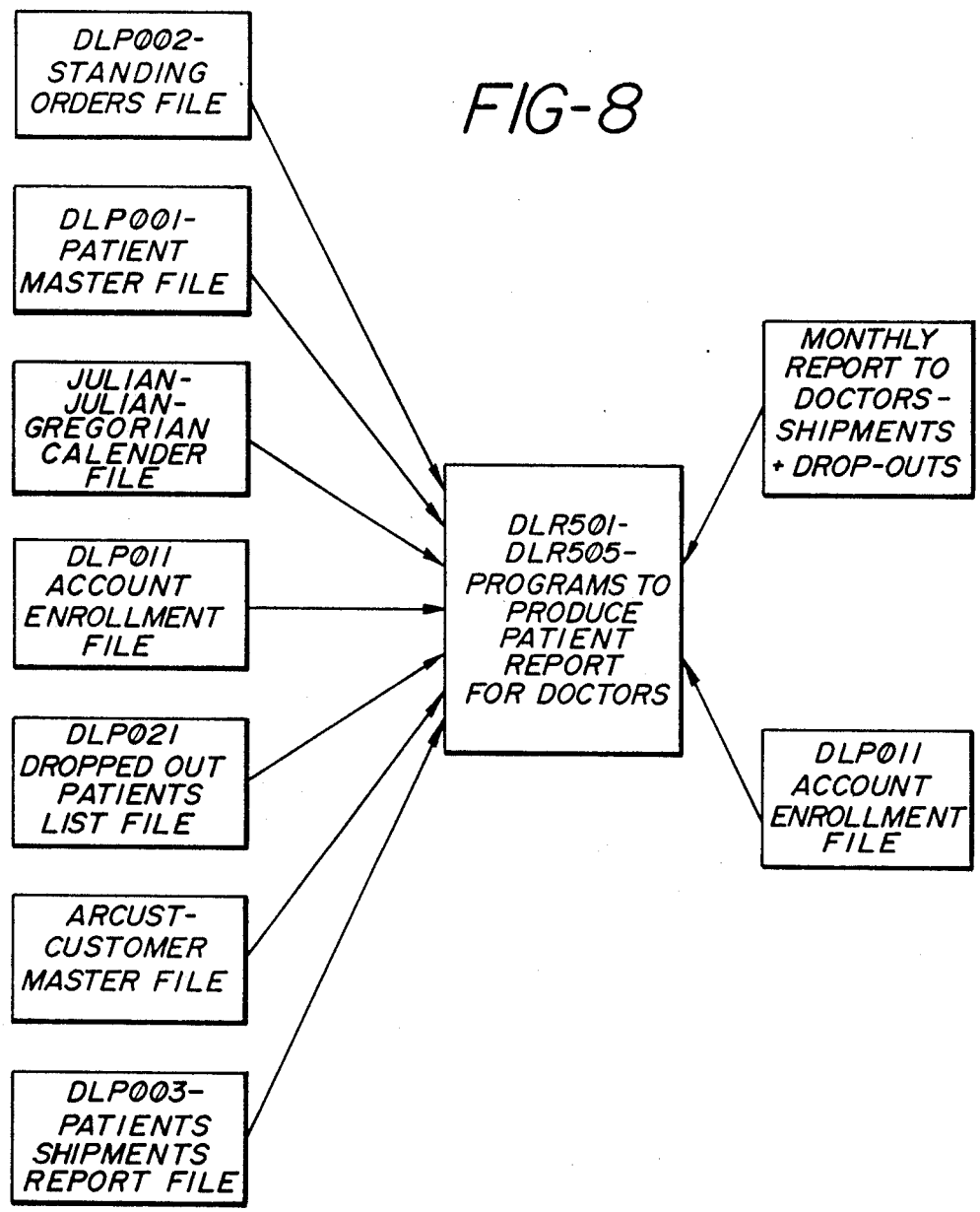

FIG. 8 shows a system flowchart for programs DLR501 through DLR505, which produce patient summary report for doctors. On the leftmost column, the various patient data and order files are provided (DLP002, DLP001, DLP021, DLP003, and ARCUST), as well as account and calendar data. Upon execution of these programs, the report itself is designated, as well as the data change to DLP011, the account enrollment file. It is noted that FIG. 8 illustrates a monthly report to be produced for the doctors, and indeed this is foreseen as most convenient in the sense of balancing date of reasonable currency along with appropriate net total amount of changes. It will be evident, however, that the self-same procedures may optionally be employed at any desired frequency, and even may, if desired, be provided for doctor access on a real-time basis. Such real time interaction is not presently foreseen as optimally desirable.

Figure 9A:
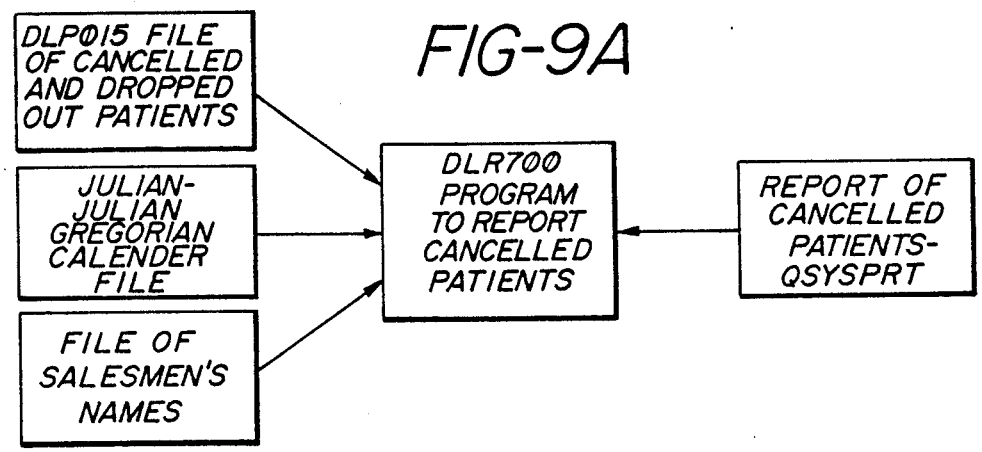
Figure 9B:
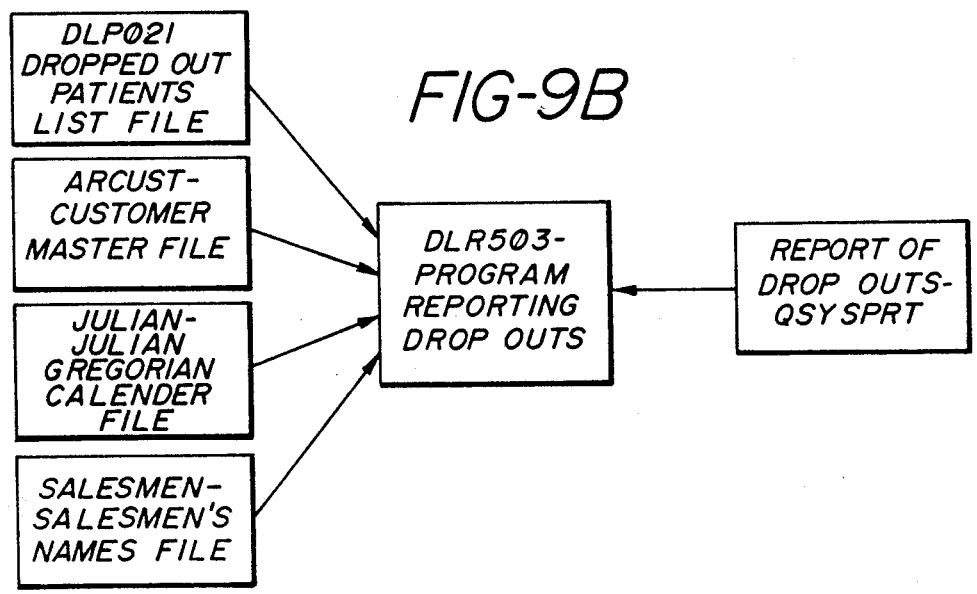
Figure 9C:
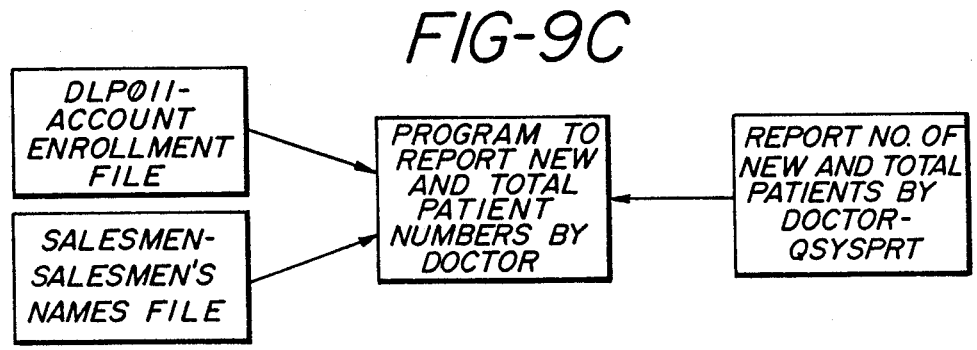

FIGS. 9A through 9C set forth system flowcharts for generating three different types of sales reports deemed advantageous for the company. In particular, FIG. 9A shows a flowchart for execution of program DLR700, the program to report cancelled patients; FIG. 9B shows a flowchart for program DLR503, a program for reporting drop-outs; and FIG. 9C shows a flowchart for a program to report new and total patient numbers, itemized by doctor. Considering the flowcharts of FIGS. 9A through 9C together, it will be appreciated that these reports are particularly directed to management of the program from the standpoint of sales, and accordingly utilize data, on the left, and provide reports, on the right, appropriate to these desires.

Figs. 10A through 10E, inclusive, set forth individual system flowcharts for utilization by the PC ordering systems set forth in general terms hereinbefore.

Figure 10A:
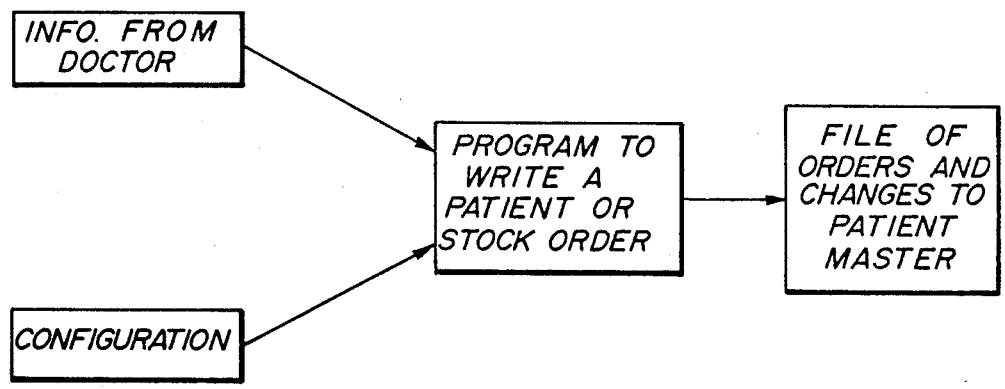
FIGS. 10a through 10d illustrate significant processing procedures at the PC's in the doctor's office and interaction with that at the company location.
Figure 10B:
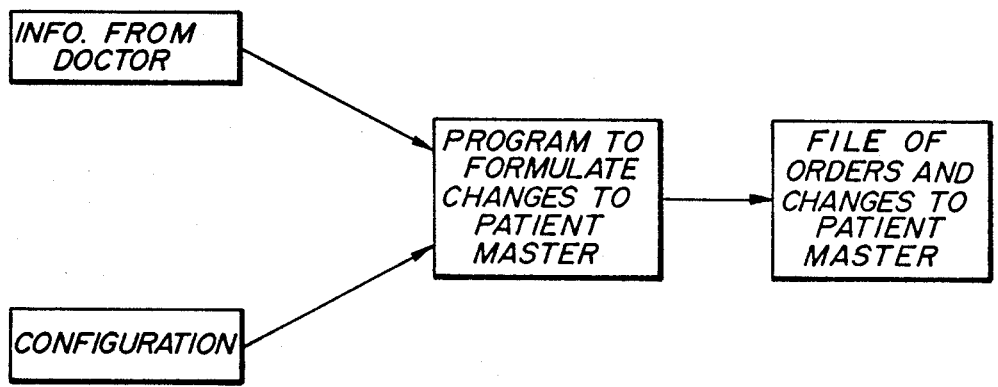
Figure 10C:
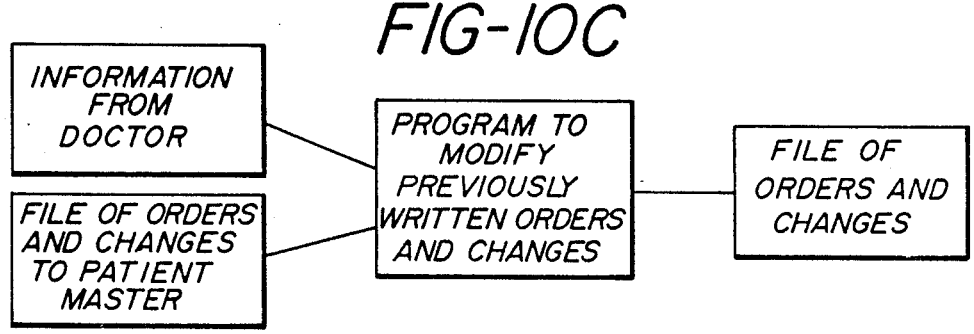

In accordance with FIG. 10A, a program to write a patient or stock order, information from the doctor is utilized in conjunction with the configuration file to generate a file of orders and changes to the patient master. FIG. 10B represents a program to formulate changes in the patient master, which utilizes information of the same character and writes information into the same file, the only difference being the essential character of the information so processed. FIG. 10C likewise outlines a program to modify previously written orders and changes, and hence uses the input information from the doctor, the standing file of orders and changes to the patient master, and simply writes new data as the doctor may desire into the file of orders and changes to the patient master.

Figure 10D:
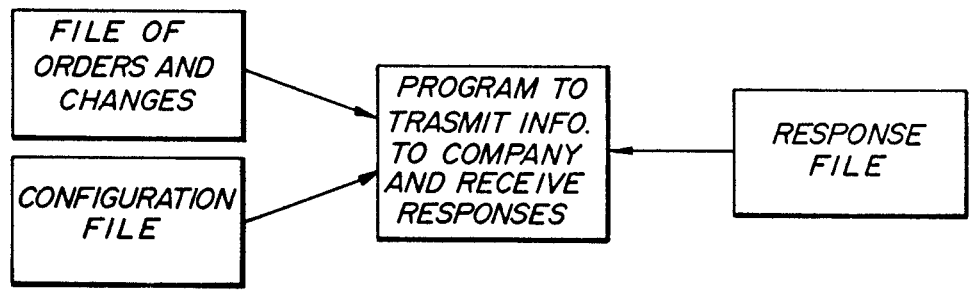
Figure 10E:

Having accumulated a file of orders and changes to the patient master in accordance with Figs. 10A, 10B, and 10C, data is transmitted to the company, and responses are received from the company, in accordance with the flowchart shown in FIG. 10D. As will be seen, the data previously developed, held in the file of orders and changes to the patient master, are combined with information from the configuration file and written at the company along with appropriate responses in the response file. Correspondingly, as set forth in FIG. 10E, a program allows the doctor to view responses from the company.

In summary, as will be appreciated from FIGS. 10A through 10E, the PC system of ordering allows the doctor, on a cumulative basis, to create a file of new orders and patient changes, to modify that file, to transmit it to the company, and to view responses from the company. It will be appreciated that PC's of the type recommended herein have substantial and elaborate computing power, and given the repository of data held at the company, the ease of data transmission through modems, and the day-to-day inclination of the designer of ordinary skill, many "ruffles and flourishes" may be added to augment the information generated by the doctor and/or communicated to the company, or vice-versa.

Figure 11:
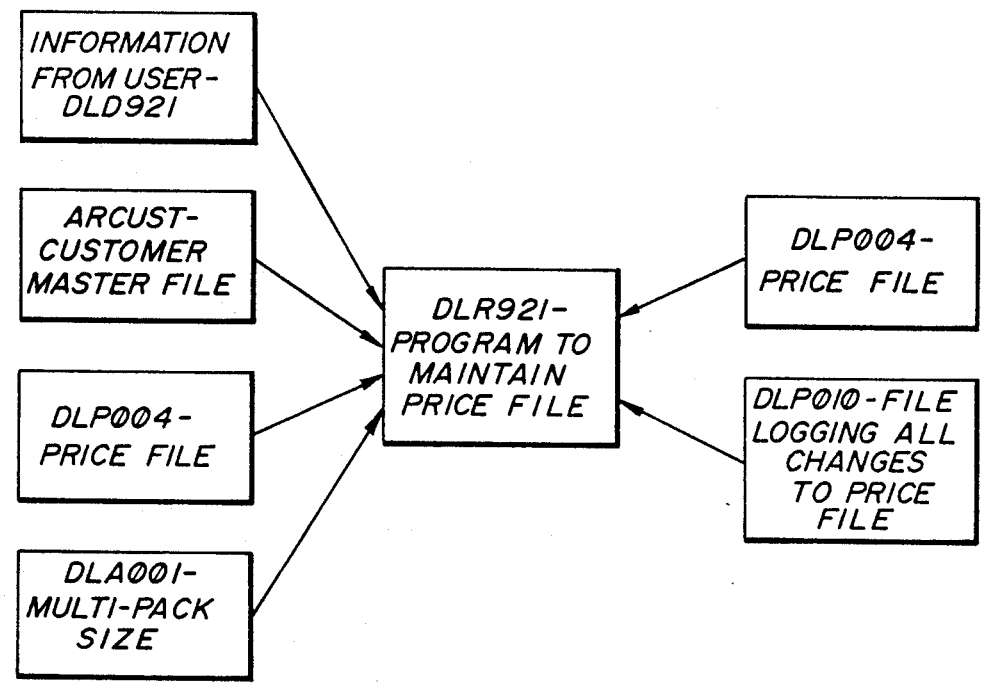

Turning finally to FIG. 11, there is shown a system flowchart for program DLR921, the program to maintain the price file. This program will be maintained with some security at the company by the company, and will allow price changes to be enacted when and as desired, thereby subsequently to provide accurate and up-to-date pricing information in accordance with the previously described functional programs for ordering, shipping, etc. As will be seen, therefore, the program DLR921 utilizes data from current files employing customer and price information, the new price information from the user, and product information, to produce an updated price file DLP004, and a record of all changes to the price file, in file DLP010.

In overview, therefore, it will be seen from the foregoing description that a best mode of practicing the invention will entail careful maintenance of numerous files, as outlined in general and detailed terms, execution on select ongoing and batch mode bases of certain programs as set forth, and generation of desired processing and shipping forms and labels, as well as sales, inventory, and the like reports. Numerous alternative embodiments, as well as modifications, will, based upon the foregoing description, be readily evident to those of ordinary skill without departing from the spirit or the scope of the principles of the present invention.

What is claimed is:

1. An integrated system for initial and ongoing supply of prescription disposable contact lenses comprising:
   central computer means including plural file storage means said plural means being respectively dedicated to predetermined data files;
   means, associated and communicating with said central computer means, for automated processing of prescription orders and prescription changes;
   distributed computing means useful by respective prescribing parties for communicating with said means for automated processing; and
   manually operable terminal means, associated and communicating with said central computer means, for manual processing of prescription orders and prescription changes;
   said central computer means further including means operable on predetermined periodicity, for initiating prescription refills for standing orders, and means for automatically integrating prescription changes with said prescription orders, and prescription refills.

2. A system as described in claim 1 and further comprising means, operable during inventory depletion associated with said integrated prescription orders and refills, for modifying data at select ones of said file storage means, whereby ongoing further orders and changes are directed based on cumulative actual current and directly forecast lens inventories.

3. A system a described in claim 1 wherein said plural file storage means comprise respective means for storing data respecting prescribing parties, means for storing data respecting patients and their lens prescriptions, means for storing data respecting standing refill orders, and means for storing data respecting lens inventories and pricing.

4. A system for provision of disposable contact lenses comprising:
  a distributed network of order entry means;
  central means, communicating with said network, for receiving and recording prescription orders;
  first means for storing a file representing new orders gathered over a predetermined time;
  second means for storing a file representing standing orders to be refilled on a periodic basis;
  means, operable on a predetermined basis, for integrating said new orders and select ones of said standing orders;
  inventory means, responsive to said means for integrating, for filling said new orders and said select standing orders;
  wherein said distributed network and said central means include mutual facility to communicate prescription changes and prescription cancellations, said system further including means for automatically amending files stored in both said means for storing, based on communicated orders, changes and cancellations;
  further including third means for storing a file of data comprehensively characterizing prescription orders, including data identifying the patient, the prescribing eye care professional, the lens prescription parameters including wear cycles, and select patient history;
  wherein said central system includes means, responsive to said third means for storing, for communicating to said eye care professional select data representing patient listing and standing prescription data.

5. A system as described in claim 4 and further including fifth means for storing a file coordinated with said third means for storing, representing lens manufacturing data and batch number traceability of lenses shipped in accordance with prior prescriptions.

6. A system is described in claim 4 wherein said means for integrating comprises means for periodically generating a batch of prescriptions to be filled during the next predetermined period, accurately specifying lenses by parameters, quantities, and location of delivery, irrespective whether the prescription has recently been ordered or changed, and in the case of standing orders, on a timely basis before the last previous prescription has been exhausted in accordance with prescribed wear cycles.

7. A system as described in claim 6 and further including fourth means for storing a file of inventory information, including respective designation of lenses committed to standing orders and lenses not so committed.

8. A system as described in claim 4 and further including means associated with said central means for establishing billing information and for communicating said billing information to select third parties for prescriptions which have been filled.

9. A system as described in claim 8 wherein said means for establishing and communicating includes sixth means for storing a file of lens pricing data, and means operably associated with said third and said sixth means for conveying billing to a select entity.

10. A system as described in claim 9 wherein said select entity is the patient or the prescribing eye care professional, or a third party reimburser, or a bank or credit agency previously authorized to pay on behalf of the patient or professional.

* * * * *